(12) United States Patent
Milam

(10) Patent No.: US 6,186,957 B1
(45) Date of Patent: Feb. 13, 2001

(54) STETHOSCOPE COVER

(76) Inventor: Michael W. Milam, 1409 Hillview Dr., Sarasota, FL (US) 34239

(*) Notice: Under 35 U.S.C. 154(b), the term of this patent shall be extended for 0 days.

(21) Appl. No.: 09/280,813

(22) Filed: Mar. 30, 1999

(51) Int. Cl.[7] ..................................................... A61B 7/02
(52) U.S. Cl. ............................................................. 600/528
(58) Field of Search ..................................... 600/528, 586

(56) References Cited

U.S. PATENT DOCUMENTS 5,592,946 * 1/1997 Eddy ..................................... 600/528
5,623,131 * 4/1997 Earnest ................................. 600/528

* cited by examiner

Primary Examiner—William E. Kamm
(74) Attorney, Agent, or Firm—Pennie & Edmonds LLP

(57) ABSTRACT

A stethoscope cover for preventing a stethoscope from being contaminated by and transmitting infectious organisms and other biohazards is made of an acoustically transmitting and viral, bacterial, and fluid impermeable material to protect the stethoscope without interfering with the normal function of the stethoscope. The cover includes a body having a front panel and a back panel. The front and back panels are joined to form a pouch with a closed distal end and an open proximal end. The pouch is configured and dimensioned to receive the head and the connector portion of the stethoscope. The cover also includes a first flap connected to one side of the proximal end of the pouch and a second flap connected to the other side of the proximal end of the pouch. The first and second flaps are configured and dimensioned to cover most of the first and second ear tubes, respectively.

11 Claims, 3 Drawing Sheets

STETHOSCOPE COVER

FIELD OF THE INVENTION

The present invention relates to a system for isolating infectious organisms, and in particular to a stethoscope cover for preventing a stethoscope from being contaminated by and transmitting infectious organisms and other biohazards.

BACKGROUND OF THE INVENTION

Resistant infectious organisms affect hospitalized patients at an ever increasing rate. Patients are frequently exposed to these organisms and other biohazards because of inadequate isolation techniques which do not maintain sufficient barriers between patients and their health care providers. Breaks in technique result in cross contamination of previously uninfected patients, which in turn, causes increased colonization and infection with resistant organisms. These infections cost millions of dollars annually and add to patient morbidity and hospital length of stay.

The primary mode of isolation in hospitals is barrier protection. Gloves are the most commonly used barrier to prevent bacterial cross contamination. Even though gloves are effective if used correctly, the need for frequent patient monitoring results in breaks in barrier protection. For example, the use of a stethoscope is a well-documented defect in isolation techniques. The stethoscope, typically a personal device owned by the health care professional, is used to assess the chest and heart of every patient by multiple health care professionals. The stethoscope is carried by each health care professional from patient to patient and acts as a fomite, increasing organism transmission. There are numerous articles documenting the harboring of organisms by the stethoscope, and the manner by which these organisms are transmitted to others.

Single-use stethoscopes have been implemented as a solution to eliminate breaks in barrier protection, but these stethoscopes are often left in the room of patients carrying resistant organisms and the supply quickly becomes contaminated. More importantly, the single-use stethoscope is hardly ever used in place of the health care professional's personal stethoscope. As a result, the single-use stethoscope has not been effective in infection control isolation and control.

As efforts to clean stethoscopes between use can be ineffective and are generally not done with consistency, there have been a number of other attempts to develop an effective and economical solution to the problem of microorganism transmission via the stethoscope. U.S. Pat. Nos. 4,867,265, 5,486,659, 5,564,431, 5,747,751, and 5,813,992 disclose a cover which only extends over the head of the stethoscope. As a result, the rest of the stethoscope remains exposed and susceptible to contamination. U.S. Pat. No. 5,623,131 discloses a two piece stethoscope cover that has a first piece which covers the head and a second piece that covers the tube that connects the head to the ear tubes. In some embodiments, there is an exposed region between to the two pieces. In the embodiment in which the two pieces are connected, the ear tubes remain exposed. Thus, even if a user properly couples the two pieces, a significant portion of the stethoscope is not covered.

U.S. Pat. No. 5,592,946 discloses a stethoscope cover that also leaves the ear tubes and the head exposed. Furthermore, this cover is made of a hypoallergenic fabric which may not be a barrier to biohazards and the only disclosed functions of the cover is to prevent allergic reactions of the wear and to decorate the stethoscope to help distract anxious patients. U.S. Pat. No. 5,466,898 discloses a stethoscope isolation system which, although completely covers the head, leaves most of the ear tubes exposed. U.S. Design Pat. No. 376,043 shows a stethoscope cover which does extend up the length of the ear tubes. This cover does not protect the side of the head of the stethoscope that contacts the patient, and, the shown design would be awkward to use.

Thus, there exists a need for improved methods for preventing the transmission of infectious organisms between patients when a stethoscope is used, and the present invention provides a solution to this problem.

SUMMARY OF THE INVENTION

The present invention relates to a protective cover for a stethoscope. The cover is made of an acoustically transmitting and viral, bacterial, and fluid impermeable material to prevent the stethoscope from being contaminated with biohazards without interference with the normal function of the stethoscope. The cover includes a body having a front panel and a back panel. The front and back panels are joined to form a pouch with a closed distal end and an open proximal end. The pouch is configured and dimensioned to receive the head and the connector portion of the stethoscope. The cover also includes a first flap connected to one side of the proximal end of the pouch and a second flap connected to the other side of the proximal end of the pouch. The first and second flaps are configured and dimensioned to cover at least the distal end of the first and second ear tubes, respectively.

Preferably, the first flap covers all of the first ear tube except for a portion proximate the ear piece of the first ear tube and the second flap covers all of the second ear tube except for a portion proximate the ear piece of the second ear tube. Each of the first and second car flaps may have a pull for handling of the cover and opening of the pouch.

In one embodiment, each of the first and second flaps has two longitudinal edges and is foldable along a center line parallel to the two longitudinal edges so that the two longitudinal edges are substantially in contact and the first and second flaps cover the respective ear tube. A crease, either with or without adhesive, may be placed along the center line to facilitate folding. Each of the first and second flaps may have a fastener to keep the two longitudinal edges substantially in contact after folding. Preferably, the fastener is perpendicular to the two longitudinal edges of the flaps and is a bendable metallic member such as a flat metal tab or metal wire.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
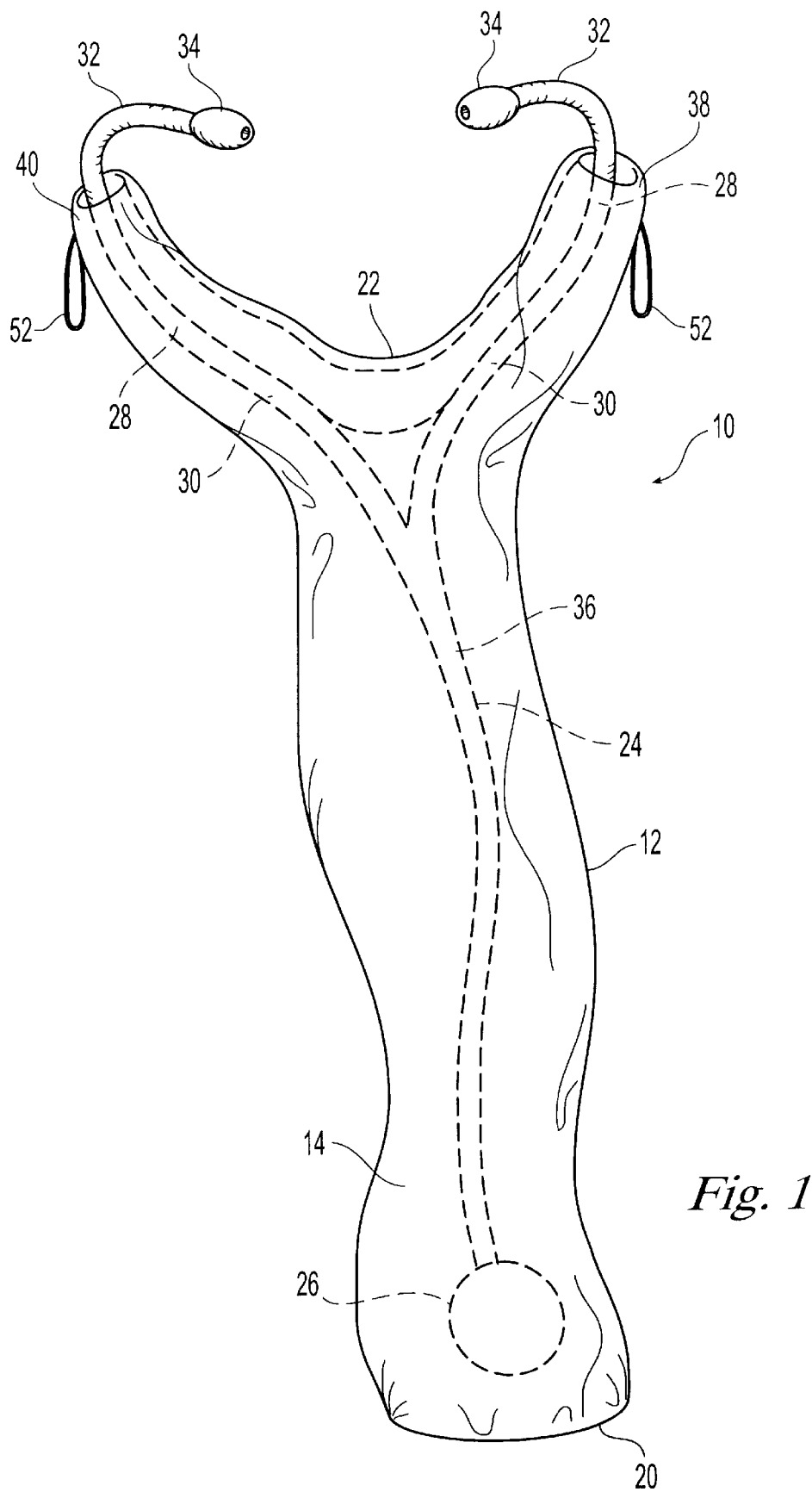
FIG. 1 shows a front view of a stethoscope cover according to the present invention with a stethoscope inserted in the cover.
Figure 2:
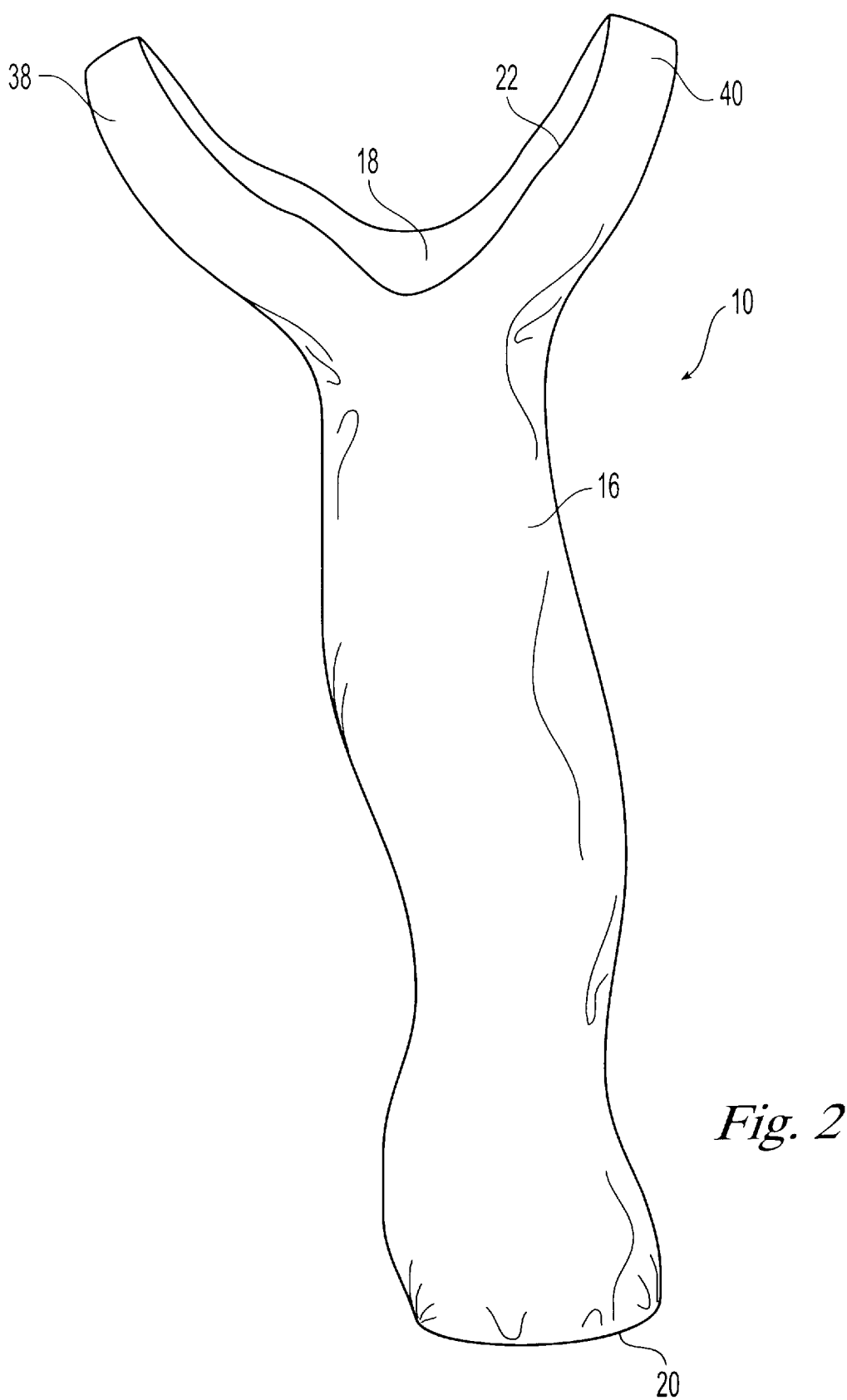
FIG. 2 shows a back view of the stethoscope cover of FIG. 1 with the stethoscope removed.

Referring to the figures, a stethoscope cover 10 according to the present invention includes a body 12 having a front panel 14 and a back panel 16. Front and back panels 14, 16 are joined to form a pouch 18 with a closed distal end 20 and an open proximal end 22. Pouch 18 is sized to receive a portion of a stethoscope 24. Specifically, stethoscope 24 has a head 26 for placing on a patient and acquiring sound, first and second ear tubes 28, each with a distal end 30 and a proximal end 32 terminating in an ear piece 34 insertable in the ear to hear the sound, and a connector section 36 connecting distal ends 30 of first and second ear tubes 28 to head 26. Pouch 18 is configured and dimensioned to receive head 26 and connector section 36 of stethoscope 24.

As cover 10 is made of a viral, bacterial, and fluid impermeable material, cover 10 prevents stethoscope 24 from being contaminated with these and other biohazards. Furthermore, the material that cover 10 is made of is also acoustically transmitting to minimize interference with the normal operation of stethoscope 24. Examples of such a material include a thin, flexible polymeric material such as polyethylene, latex rubber, silicone, soft vinyl, urethane, cellophane, and the like. These are the same materials that are used for gloves and other protective garments and are well known in the art. There are a number of ways that front and back panels 14, 16 can be joined together to form pouch 18 so that an tight seal between the two is formed. For example, front and back panels 14, 16 can be welded or glued at their edges.

In order to prevent exposure of ear tubes 28 to biohazards, stethoscope cover 10 also includes a first flap 38 connected to a first side of proximal end 22 of pouch 18 which covers at least distal end 30 of first ear tube 28 and a second flap 40 connected to a second side of proximal end 22 of pouch 18 which covers at least distal end 30 of second ear tube 28. Preferably as shown in FIG. 1, first flap 38 covers all of first ear tube 28 except for a portion proximate ear piece 34 of first ear tube and second flap 40 covers all of second ear tube 28 except for a portion proximate ear piece 34 of second ear tube 28. First and second flaps 38, 40 can be integral with body 12 or can be joined to body 12 in such a fashion that there is a tight seal between body 12 and first and second flaps 38, 40.

Figure 3:
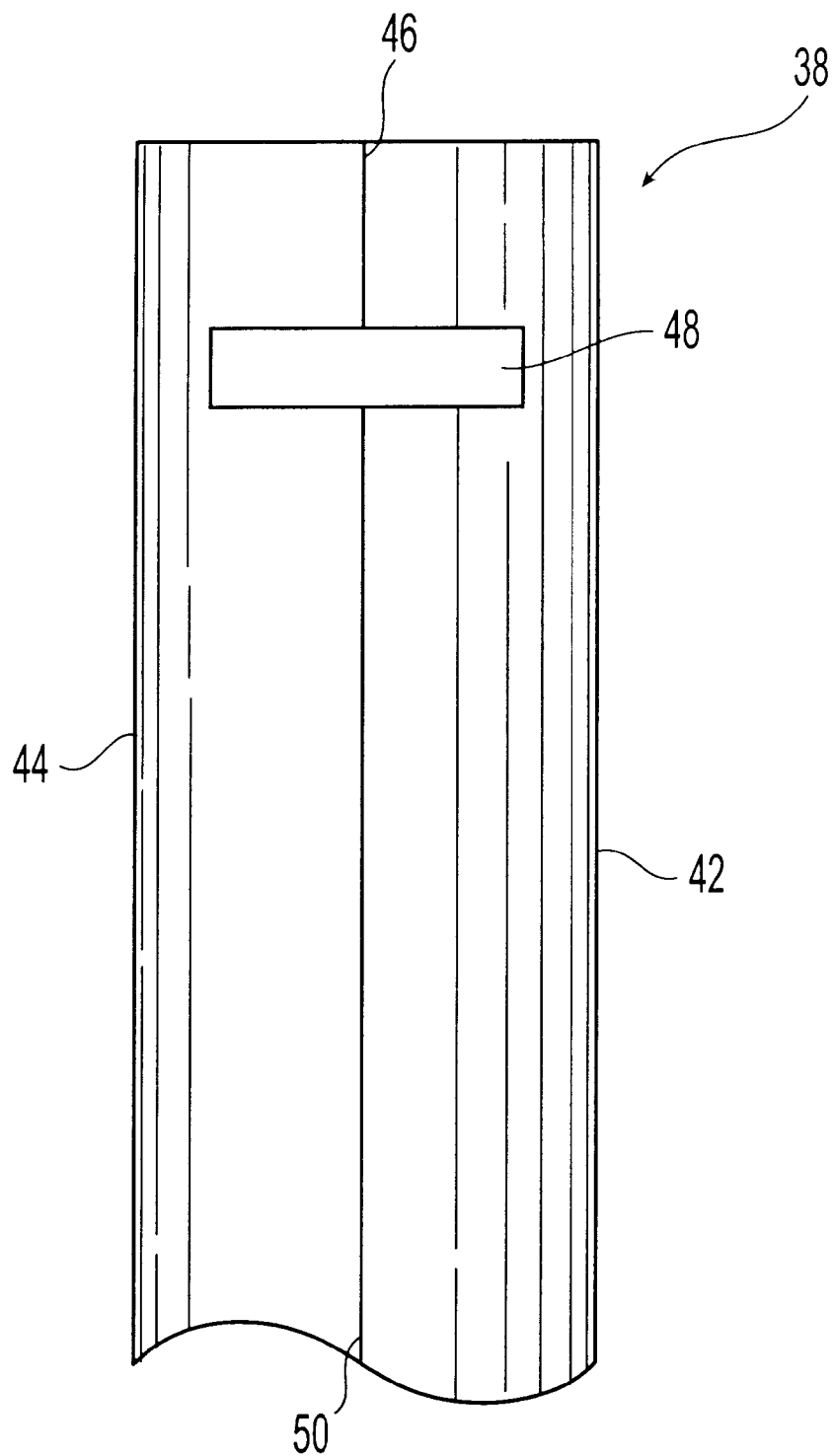
FIG. 3 shows a front view of a proximal portion of a first flap of the stethoscope cover, the second flap being identical.

Each of the first and second flaps 38, 40 has two longitudinal edges 42, 44 and is foldable along a center line 46 which is parallel to longitudinal edges 42, 44. When first and second flaps 38, 40 are folded along center line 46, longitudinal edges 42, 44 are substantially in contact and first and second flaps 38, 40 cover most of ear tubes 28. As shown in FIG. 3, first and second flaps 38, 40 have a fastener 48 to keep longitudinal edges 42, 44 substantially in contact (and, as a result, to cover first and second car tubes 28, 30). As explained below, fastener 48 should have sufficient holding power to keep longitudinal edges 42, 44 together during normal use, yet should not have holding power which would prevent removal of cover 10 from stethoscope 24 after use. Preferably, fastener 48 is a bendable metallic member, such as a flat metal tab or a metal wire, which is perpendicular to longitudinal edges 42, 44 and bends when first and second flaps 38, 40 are folded.

First and second flaps 38, 40 can be provided with a crease 50 along center line 46 to facilitate folding. In order to assist in maintaining substantial contact between longitudinal edges 42, 44, at least a portion of crease 50 may have an adhesive. Because the adhesive is at or near crease 50, the adhesive should not prevent separation of cover 10 from stethoscope 24 when desired.

In use, a health care professional having a clean stethoscope hanging from her neck takes a stethoscope cover 10 from a supply of covers. In order to make the covers readily accessible and to increase user compliance, the supply can be conveniently located, e.g. near a box of examination gloves on an isolation cart. Pouch 18 can be shaken opened in much the same manner that a grocery bag is opened. First and second flaps 38, 40 are an ideal location to hold cover 10 while pouch 18 is opened for insertion of the stethoscope in cover 10. In this regard, first and second flaps 38, 40 can be provided with a pull 52 to further facilitate opening of pouch 18. Cover 10 is slid over stethoscope until all of head 26 and connector section 36 is within pouch 18. First and second flaps 38, 40 are folded so that first and second ear tubes 28 are entirely covered except for a portion near ear pieces 34. As both cover 10 and stethoscope 24 are clean, it does not matter if the health care professional dons gloves before or after cover 10 is placed on stethoscope 24 (assuming the health care professional has washed hands). For optimal results, gloved hands should be used to grasp the covered first and second ear tubes 28 and place ear pieces 34 in the ears.

Once ear pieces 34 are inserted in the ears, the patient can be examined. Stethoscopes can be provided with a head that is a bell-shaped member which amplifies sound, a diaphragm on a ring responsive to sound, or a combination bell/diaphragm in which the mode of use is selected with a valve. Front panel 14 and/or back panel 16, or a portion of either, can be made of a translucent or transparent material so that head 26 can be visualized through cover 10. Even though cover 10 is made of a material such that tactile feel of stethoscope 24 through cover 10 would be sufficient for use and manipulation of stethoscope 24, making either of the panels or a portion of the panels of a translucent or transparent material would be desirable to visualize a valve of a combination head. Furthermore, pouch 18 is wide enough to allow head 26 to spin around so that the bell or diaphragm can be appropriately positioned through cover 10.

After examination of the patient, ear pieces 34 are removed from the ears with gloved hands and cover 10 is pulled down off of stethoscope 24. In this regard, if cover 10 is provided with pull 52, pull 52 can be used to separate first and second flaps 38, 40 from first and second ear tubes 28. The used cover 10 can be discarded along with the contaminated gloves.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A protective cover for a stethoscope having a head, first and second ear tubes, each of the tubes having a distal end and a proximal end terminating in an ear piece insertable in an ear, and a connector section connecting the distal ends of the first and second ear tubes to the head, the cover comprising:

a body having a front panel and a back panel, the front and back panels joined to form a pouch with a closed distal end and an open proximal end, the pouch configured and dimensioned to receive the head and the connector portion of the stethoscope;

a first flap connected to a first side of the proximal end of the pouch and configured and dimensioned to cover at least the distal end of the first ear tube; and a second flap connected to a second side of the proximal end of the pouch and configured and dimensioned to cover at least the distal end of the second ear tube, wherein the cover is made of an acoustically transmitting and viral, bacterial, and fluid impermeable material.

2. The protective cover of claim 1 wherein the first flap covers all of the first ear tube except for a portion proximate the ear piece of the first ear tube; and the second flap covers all of the second ear tube except for a portion proximate the ear piece of the second ear tube.

3. The protective cover of claim 1 wherein each of the first and second flaps has two longitudinal edges and is foldable along a center line parallel to the two longitudinal edges so that the two longitudinal edges are substantially in contact and the first and second flaps cover the respective ear tube.

4. The protective cover of claim 3 wherein each of the first and second flaps has a fastener to keep the two longitudinal edges substantially in contact after folding.

5. The protective cover of claim 4 wherein the fastener is perpendicular to the two longitudinal edges.

6. The protective cover of claim 5 wherein the fastener is a bendable metallic member.

7. The protective cover of claim 6 wherein the metallic member is a flat metal tab.

8. The protective cover of claim 6 wherein the metallic member is a metal wire.

9. The protective cover of claim 3 wherein each of the first and second flaps has a crease along the center line to facilitate folding.

10. The protective cover of claim 9 wherein each crease has adhesive along at least a portion of the crease for maintaining contact between the respective two longitudinal edges.

11. The protective cover of claim 1 wherein each of the first and second ear flaps has a pull for handling of the cover and opening of the pouch.

* * * * *